US009320696B2

(12) United States Patent
Wang et al.

(10) Patent No.: US 9,320,696 B2
(45) Date of Patent: Apr. 26, 2016

(54) ORAL CARE COMPOSITIONS AND METHODS

(71) Applicant: Colgate-Palmolive Company, New York, NY (US)

(72) Inventors: Wei Wang, Plainsboro, NJ (US); Virginia Barnes, Ringoes, NJ (US); Harsh M. Trivedi, Hillsborough, NJ (US); Tao Xu, Newton, MA (US)

(73) Assignee: Colgate-Palmolive Company, New York, NY (US)

( * ) Notice: Subject to any disclaimer, the term of this patent is extended or adjusted under 35 U.S.C. 154(b) by 34 days.

(21) Appl. No.: 14/505,496

(22) Filed: Oct. 2, 2014

(65) Prior Publication Data

US 2015/0086490 A1    Mar. 26, 2015

Related U.S. Application Data

(62) Division of application No. 13/518,103, filed as application No. PCT/US2010/061491 on Dec. 21, 2010, now Pat. No. 8,883,179.

(60) Provisional application No. 61/288,359, filed on Dec. 21, 2009.

(51) Int. Cl.
| | |
|---|---|
| *A61Q 11/00* | (2006.01) |
| *A61K 31/27* | (2006.01) |
| *A61K 31/265* | (2006.01) |
| *A61K 36/45* | (2006.01) |
| *A61K 8/42* | (2006.01) |
| *C07C 69/96* | (2006.01) |
| *A61K 36/324* | (2006.01) |
| *C07C 271/38* | (2006.01) |
| *A61K 8/97* | (2006.01) |
| *A61K 31/05* | (2006.01) |
| *A61K 31/19* | (2006.01) |
| *A61K 8/34* | (2006.01) |
| *A61K 8/368* | (2006.01) |
| *A61K 8/37* | (2006.01) |

(52) U.S. Cl.
CPC . *A61K 8/42* (2013.01); *A61K 8/347* (2013.01); *A61K 8/368* (2013.01); *A61K 8/97* (2013.01); *A61K 31/05* (2013.01); *A61K 31/19* (2013.01); *A61K 31/265* (2013.01); *A61K 31/27* (2013.01); *A61K 36/324* (2013.01); *A61K 36/45* (2013.01); *A61Q 11/00* (2013.01); *C07C 69/96* (2013.01); *C07C 271/38* (2013.01); *A61K 8/37* (2013.01)

(58) Field of Classification Search
CPC ....... A61K 31/05; A61K 31/19; A61K 36/45; A61K 8/97; A61K 8/42; A61K 8/368; A61K 31/27; A61K 36/324; A61K 8/347; A61K 31/265; A61K 8/37; C07C 69/96; C07C 271/38; A61Q 11/00
USPC ............. 424/49, 732; 514/491, 512
See application file for complete search history.

(56) References Cited

U.S. PATENT DOCUMENTS

| | | | |
|---|---|---|---|
| 5,830,915 A | 11/1998 | Pikul et al. | |
| 5,840,322 A | 11/1998 | Weiss et al. | |
| 6,716,883 B1 | 4/2004 | Casper et al. | |
| 6,765,003 B1 | 7/2004 | Mantegani et al. | |
| 2007/0053851 A1 | 3/2007 | Maillan et al. | |
| 2009/0087501 A1 | 4/2009 | Cummins | |
| 2012/0014884 A1* | 1/2012 | Trivedi | A61K 8/375 424/54 |

FOREIGN PATENT DOCUMENTS

| | | |
|---|---|---|
| CA | 2312505 | 12/2001 |
| DE | 202006008905 | 8/2006 |
| FR | 9805673 | 11/1999 |
| JP | H11-139947 | 5/1999 |
| JP | 2001-512713 | 8/2001 |
| RU | 2170232 | 7/2001 |
| WO | WO 98/03166 | 1/1998 |
| WO | WO 98/15525 | 4/1998 |
| WO | WO 2007/011674 | 1/2007 |
| WO | WO 2008/115783 | 9/2008 |
| WO | WO 2008/120220 | 10/2008 |
| WO | WO 2009/045952 | 4/2009 |
| WO | WO 2009/144179 | 12/2009 |
| WO | WO 2010/120275 | 10/2010 |

OTHER PUBLICATIONS

Birkedal-Hansen et al., 1993, "Matrix Metalloproteinases: A Review", Critical Reviews in Oral Biology and Medicine 4(2):197-250.
Bodet et al., 2006, "Inhibition of Periodontopathogen-derived Proteolytic Enzymes by a High-molecular-weight Fraction Isolated from Cranberry", Journal of Antimicrobial Chemotherapy 57(4):685-690.
Bodet et al., 2006, "Anti-inflammatory Activity of a High-molecular-weight Cranberry Fraction on Macrophages Stimulated by Lipopolysaccharides from Periodontopathogens", Journal of Dental Research 85(3):235-239.
Casper et al., 1999, "Resveratrol has Antagonist Activity on the Aryl Hydrocarbon Receptor: Implications for Prevention of Dioxin Toxicity", Molecular Pharmacology 56:784-790.
Golub et al., 1998, "Modulation of the Bost Response in the Treatment of Periodontitis", Dentistry Today 17(10):102-106, 108-109.
Hernandez et al., 2007, "MMP-13 and TIMP-1 Determinations in Progressive Chronic Periodontitis", Journal of Clinical Periodontology 34(9):729-735.
Hess et al., 2001, "AP-1 and Cbfa/Runt Physically Interact and Regulate Parathyroid Hormone-dependent MMP13 Expression in Osteoblasts through a New Osteoblast-specific Element 2/AP-I Composite Element", Journal of Biological Chemistry 276(23):20029-20038.
Ilgenli et al., 2006, "Gingival Crevicular Fluid Matrix Metalloproteinase—13 Levels and Molecular Forms in Various Types of Periodontal Diseases", Oral Diseases 12:573-579.
Kiili et al., 2002, "Collagenase-2 (MMP-8) and Collagenase-3 (MMP-13) in Adult Periodontitis: Molecular Forms and Levels in Gingival Crevicular Fluid and Immunolocalisation in Gingival Tissue", Journal of Clinical Periodontology 29:224-232.
Kiili et al., 2004, Erratum in Journal of Clinical Periodontology 31(2):149.

(Continued)

*Primary Examiner* — Brian-Yong Kwon
*Assistant Examiner* — Miriam A Levin

(57) ABSTRACT

Described herein are compositions comprising a MMP-13 inhibitor, and methods of using the same.

8 Claims, No Drawings

(56) References Cited

OTHER PUBLICATIONS

La et al., 2009, "Cranberry Proanthocyanidins Inhibit MMP Production and Activity", Journal of Dental Research 88(7):627-632.
PCT/US2010/061491—ISR and Written Opinion mailed Sep. 13, 2011.
PCT/US2010/061491—Written Opinion mailed Feb. 8, 2012.
Qin et al., 2003, "Gene Expression Profiles and Transcription Factors Involved in Parathyroid Hormone Signaling in Osteoblasts Revealed by Microarray and Bioinformatics", Journal of Biological Chemistry 278(22):19723-19731.
Singh et al., 2000, "Inhibition of Dioxin Effects on Bone Formation in vitro by a Newly Described Aryl Hydrocarbon Receptor Antagonist, Resveratrol", Journal of Endocrinology 167:183-195.
Soleas et al., 1997, "Resveratrol: a Molecule Whose Time Has Come? And gone?", Clinical Biochemistry 30(2):91-113.
Tervahartiala et al., 2000, "The in vivo Expression of the Collagenolytic Matrix Metalloproteinases (MMP-2, -8, -13, and -14) and Matrilysin (MMP-7) in Adult and Localized Juvenile Periodontitis", Journal of Denial Research 79(12):1969-1977.
Uitto et al., 1998, "Collagenase-3 (Matrix Metalloproteinase-13) Expression is Induced in Oral Mucosal Epithelium During Chronic Inflammation", American Journal of Pathology 152(6):1489-1499.
Weiss et al., 1998, "Inhibiting Interspecies Coaggregation of Plaque Bacteria with a Cranberry Juice Constituent", Journal of the American Dental Association 129:(12)1719 -1723.
Weiss et al., 2004, "A High Molecular Mass Cranberry Constituent Reduces Mutans Streptococci Level in Saliva and Inhibits in vitro Adhesion to Hydroxyapatite", FEMS Microbiology Letters 232:89-92.

* cited by examiner

ORAL CARE COMPOSITIONS AND METHODS

CROSS REFERENCE TO RELATED APPLICATIONS

This application is a divisional of U.S. patent application Ser. No. 13/518,103, filed 12 Jul. 2012, which is a national stage entry under 35 U.S.C. §371 of International Patent Application No. PCT/US2010/061491, filed 21 Dec. 2010, which claims priority to U.S. Provisional Patent Application No. 61/288,359, filed on 21 Dec. 21 2009, the entireties of which are incorporated herein by reference.

BACKGROUND

Matrix metalloproteinases, which are referred to as MMPs, are a naturally occurring family of calcium- and zinc-dependent endopeptidases that are found in most mammals. Overexpression and activation of MMPs or an imbalance between MMPs and inhibitors of MMPs have been suggested as factors in the pathogenesis of diseases characterized by the breakdown of extracellular matrix or connective tissues.

The major component of periodontium cementum, periodontal ligament and alveolar bone) is organic matrix. Matrix metalloproteinases (MMPs) are involved in remodelling the periodontal matrix. Destructive MMPs degrade various components of the extracellular matrix both in physiological and pathological conditions. The pathologic overproduction of destructive MMPs leads to an inappropriate and excessive degradation of matrix. The overproduction of destructive MMPs facilitates bone resorption by first degrading osteoid (the nonmineralized and newly synthesized bone matrix) and then degrading the matrix, resulting in the clinical manifestations of periodontitis including gingival recession, pocket formation, loss of attachment, tooth mobility and tooth loss.

MMP-13 is one of the major destructive MMPs that plays a role in degradation of the extracellular matrix. The level of MMP-13 expression correlates to periodontitis clinical indexes. MMP-13 is detected in diseased periodontal tissue and in gingival crevicular fluid; however, MMP-13 is not detected in healthy oral mucosa. Uitto et al. *American Journal of Pathophysiology*, 152(6), 1489 (1998).

Matrix metalloproteinase-13 was known as an enzyme responsible for bone resorption and cartilage destruction in rheumatoid arthritis and osteoarthritis. Elevated levels of MMP-13 are also known to exist in gingival crevicular fluid of patients with chronic periodontitis. In addition, MMP-13 is known to contribute to both bone and connective tissue destruction in patients with periodontal diseases. Ilgenli, T. et al. *Oral Diseases*, 12, 573 (2006).

Currently, antimicrobials, nonsteroidal anti-inflammatory agents (NSAIDs), bisphosphonates and tetracyclines used in the treatment of periodontal disease. These agents often do not provide adequate symptomatic relief and are not believed to alter the natural progression of the disease. Furthermore, powerful side effects are found with most all of these therapies. Hence, there is a great need for safe and effective therapy for these disorders.

Although there are many treatments for various aspects of periodontal disease, there remains a need to develop an improved oral composition comprising active ingredients which target destructive MMPs that facilitate bone resorption and cause tissue breakdown. In particular, there is a need to develop improved oral compositions which target MMP-13, which contributes to both bone resorption and connective tissue destruction.

SUMMARY

In a first aspect, a method for the inhibition of matrix metalloproteinase MMP-13 comprising administering to a subject an effective therapeutic amount of a matrix metalloproteinase MMP-13 inhibitor, wherein the matrix metalloproteinase MMP-13 inhibitor is selected from the group consisting of cranberry extract NDM, acetyl keto β-boswellic acid, resveratrol, 2-isopropyl-5-methylcyclohexyl 2-hydroxyphenylcarbamate, 4-acetamidophenyl 2-isopropyl-5-methylcyclohexyl carbonate, and combinations thereof.

The method provides a new mechanism for effectively inhibiting matrix metalloproteinase MMP-13 and thereby treating or preventing conditions caused by MMP-13 expression. The present inventors have surprisingly found that cranberry extract NDM, acetyl keto β-boswellic acid (AKBBA), resveratrol, 2-isopropyl-5-methylcyclohexyl 2-hydroxyphenylcarbamate, 4-acetamidophenyl 2-isopropyl-5-methylcyclohexyl carbonate, and combinations thereof, effectively inhibit matrix metalloproteinase MMP-13.

In a second aspect, an oral care composition, the composition comprising an orally acceptable carrier and a compound selected from the group consisting of cranberry extract non-dialyzable material, acetyl keto β-boswellic acid, resveratrol, 2-isopropyl-5-methylcyclohexyl 2-hydroxyphenylcarbamate, 4-acetamidophenyl 2-isopropyl-5-methylcyclohexyl carbonate, and combinations thereof, wherein the compound is present in an amount effective to inhibit MMP-13.

In a third aspect, an oral care composition comprising a compound selected from the group consisting of cranberry extract non-dialyzable material, acetyl keto β-boswellic acid, resveratrol, 2-isopropyl-5-methylcyclohexyl 2-hydroxyphenylcarbamate, 4-acetamidophenyl 2-isopropyl-5-methylcyboxyl carbonate, and combinations thereof for the treatment or prevention of a condition caused by MMP-13 expression.

Also, a method of treating degradation of the extracellular matrix, loss of attachment, tooth loss, tooth mobility, pocket formation and bone loss.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein "flavorant" refers to any material or mixture of materials that enhances the taste of a composition.

Compositions

In some embodiments, a composition comprising a therapeutically effective amount of a MMP-13 inhibitor and an orally acceptable carrier. In some embodiments, the MMP-13 inhibitor is selected from the group consisting of cranberry extract non-dialyzable material, acetyl keto β-boswellic acid, resveratrol, 2-isopropyl-5-methylcyclohexyl 2-hydroxyphenylcarbamate, 4-acetamidophenyl 2-isopropyl-5-methylcyclohexyl carbonate, and a combination of two or more thereof.

In some embodiments, the MMP-13 inhibitor is selected from the group consisting of cranberry extract non-dialyzable material, acetyl keto β-boswellic acid, resveratrol, 2-isopropyl-5-methylcyclohexyl 2-hydroxyphenylcarbamate, 4-acetamidophenyl 2-isopropyl-5-methylcyclohexyl carbonate, and a combination of two or more thereof.

In some embodiments, the composition further comprises an anti-plaque agent, a whitening agent, antibacterial agent, cleaning agent, a flavoring, agent, a sweetening agent, an adhesion agent, a surfactant, a foam modulator, an abrasive, a pH modifying agent, a humectant, a mouth feel agent, a colorant, a tartar control (anticalculus) agent, a fluoride ion source, a saliva stimulating agent, a nutrient, or a combination of two or more thereof.

Some embodiments further comprise a sweetening agent, alcohol, glycerin, sorbitol propylene glycol, polyethylene glycol, a polymer, alkyl polyglycoside (APG), polysorbate, castor oil, or menthol.

In some embodiments, the sweetening agent is saccharin or sodium saccharin. In some embodiments, the alcohol is ethanol. In some embodiments, the polymer is POLOXAMER® 407 or PLURONIC® F108 (both available from BASF Corporation). In some embodiments, the polyethylene glycol is PEG40.

Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethote, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition. These may include agglomerated silica particles that are designed to break down with agitation, such as SORBOSIL® BFG series, (e.g., BFG 10, BFG 50, BFG 100, etc.), CBT60S, CBT70, or AC33/43 silicas, commercially available from PQ Corporation, Valley Forge, Pa.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

In certain embodiments, the compositions can further comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In certain embodiments, the compositions optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate and phosphonoalkane carboxylic acids. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In certain embodiments, the compositions optionally comprise a fluoride ion source and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof. One or more fluoride ion sources are optionally present in an amount providing a clinically efficacious amount of soluble fluoride ion to the oral composition.

In certain embodiments, the compositions optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In certain embodiments, the compositions optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, methionine, threonine, levocarnitine and L-carnitine), lipotropics such as choline, inositol, betaine, and linoleic acid), and mixtures thereof.

In various embodiments, the oral composition according is not intentionally swallowed, but is rather retained in the oral cavity for a time sufficient to effect the intended utility. In other portable embodiments (such as a lozenge, mint, bead, wafer, liquid formulated for oral application from a small portable nebulizer, liquid formulated for oral application from a small portable drop-generating bottle, or a soft pliable tablet), the oral composition is intentionally swallowed, optionally after retention in the oral cavity for a time sufficient to effect intended utility.

The oral care compositions of the various embodiments preferably are in the form of a dentifrice. The term "dentifrice" as used throughout this description, denotes a paste, gel, or liquid formulation. The dentifrice may be in any desired form, such as toothpaste; (including deep striped, surface striped, multi-layered, having a gel surround the paste); powder; beads; mouthwash; mouth rinses; lozenge; dental gel; a periodontal gel; a liquid suitable for painting a dental surface; a chewing gum; a dissolvable, partially dissolvable or non-dissolvable film or strip; a wafer; a wipe or towelette; an implant; a foam; a troche; a dental floss, liquid formulated for oral application in a small portable nebulizer (spray bottle), liquid formulated for oral application in a small portable drop-generating, bottle, a soft pliable tablet ("chewie"), or any combinations thereof. As used herein, an "orally acceptable carrier" refers to a material or combination of materials that are safe for use in the compositions, commensurate with a reasonable benefit/risk ratio.

As used herein the terms "orally acceptable vehicle" or "orally acceptable carrier" refer to any vehicle useful in formulating any of the dentifrices described above. Suitable orally acceptable vehicles include, for example, one or more of the following: a solvent, an alkaline agent, a humectant, a thickener, a surfactant, an abrasive, an anti-calculus agent, a colorant, a flavoring agent, a dye, a potassium containing salt, an anti-bacterial agent, desensitizing agents, stain reducing agents, and mixtures thereof.

Some embodiments also provide a composition selected from the group consisting of: a lozenge, a mint, a bead, a wafer, a small portable nebulizer containing said admixture in liquid formulated for oral application as a spray, a small portable bottle containing said admixture in liquid formulated for oral application as a drop, and a soft pliable tablet.

The cranberry extract non-dialyzable material (NDM) is derived from cranberry juice concentrate. Cranberry juice contains high molecular weight materials (NDM) that inhibit bacterial adhesion to host cells as well as the co-aggregation of many oral bacteria. The cranberry extract NDM was prepared according to a method described by Weiss E; Lev-Dor, R.; Kashmann, Y.; Goldhar, J.; Sharon, N.; Ofek, Itzhak, *J. Am. Dent. Assoc.* 129, 1719 (1998).

Acetyl keto β-boswellic acid (AKBBA) is a useful active compound isolated from the *Boswellia* plant which exhibits antibacterial, anti-inflammatory and antioxidant activities. *Boswellia* is a genus of trees that produce extracts having anti-inflammatory properties, including boswellic acid compounds. For example, *Boswellia sacra, B. frereana; B. serrata*; and *B. papyrifera* and their sub-species produce suitable extracts.

Resveratrol (3,5,4'-trihydroxystilbene), the parent compound of a family of molecules including glucosides and polymers, is a potent AhR antagonist as described in French Patent Application No. 9805673 filed May 5, 1998. It is an anti-fungal agent or phytoalexin produced by plants classified as spermatophytes of which vines, peanuts and pines are prime representatives (Soleas et al., 1997, *Clin Biochemistry*, 30:91-113). As an AhR antagonist, resveratrol, the chemical name of which is 3,5,4'-trihydroxystilbene, is useful generally to prevent the toxic effects of environmental exposure to AhR ligands, including, for example, halogenated and polycyclic aryl hydrocarbons, polyaromatic hydrocarbons and polychlorinated biphenyls. In addition, resveratrol has been demonstrated to prevent the induction of the proinflammatory cytokine, IL-1 Beta, by AhR ligands (Casper et al. 1999, *Molecular Pharmacology*, 56:784-790).

Methods of Use

Some embodiments provide methods for treating conditions associated with aberrant MMP-13 expression, comprising administering to an animal, in need thereof, a therapeutically effective amount of a MMP-13 inhibitor. In some embodiments, the composition is suitable for administration or application to the oral cavity of an animal.

In some embodiments, provided is the use of a MMP-13 inhibitor in the manufacture of a medicament for treating conditions associated with aberrant MMP-13 expression.

In other embodiments, the MMP-13 inhibitor is selected from the group consisting of cranberry extract NDM, acetyl keto β-boswellic acid, resveratrol, 2-isopropyl-5-methylcyclohexyl 2-hydroxyphenylcarbamate and 4-acetamidophenyl 2-isopropyl-5-methylcyclohexyl carbonate, or a combination of two or more thereof. In some embodiments, the condition associated with MMP-13 expression is selected from periodontal disease, degradation of the extracellular matrix, tooth mobility, tooth decay, loss of attachment, tooth loss, pocket formation or bone loss.

EXAMPLES

Parathyroid hormone (PTH) stimulates the transcription of MMP-13. The experimental method utilizes PTH to stimulate MMP-13 transcription in UMR 106-01 cells, which are cells derived from a rat osteoblastic cell line. The UMR 106-01 cell line provides useful model system for studying effects of PTH on osteoblasts in vitro. See, e.g., Qin, L. et al. *Journal of Biological Chemistry*, 278(22), 19723 (2003).

Material

Parathyroid hormone (rat PTH 1-34) was purchased from Sigma.

Cell Culture

The UMR 106-01 cells were cultured in Eagle's minimal essential medium (EMEM) supplemented with 25 mM Hepes 7.4, 1% nonessential amino acids, 100 units/ml penicillin, 100 μg/ml streptomycin and 5% fetal bovine serum.

Real Time Quantitative RT-PCR

UMR 106-01 cells were seeded in 12-well plates and cultured for 2-3 days in cell culture media. When cells were confluent, the cell culture media was changed to 1% fetal bovine serum (not 5% fetal bovine serum) for overnight cell starvation. The cells were preincubated with active ingredient for 15 min and then incubated with PTH ($10^{-8}$ M) for 4 hours.

Total RNA from UMR 106-01 cells stimulated with or without PTH was isolated with TRIzol reagent. Total RNA (0.1 µg) was reverse-transcribed to cDNA with the Invitrogen Superscript kit according to the manufacturer's instructions. PCR was performed on cDNA using primers, and the sequences used are listed below. All were amplified by adding 2.5 µl of cDNA to the PCR mixture (22.5 µl) containing each primer (0.2 µM) and 12.5 µl of the Platinum SYBR Green qPCR SuperMix UDG (Invitrogen). The reactions were pre-incubated at 50° C. for 2 minutes for decontamination of dU-containing DNA by UDG, then at 95° C. for 2 minutes to inactivate UDG and activate Taq. The PCR program continued for 49 cycles of denaturation at 95° C. for 15 seconds, annealing and elongation of the primers at 60° C. for 30 seconds. Relative quantification of gene expression was determined by using the 2-delta delta CT method where fold changes in gene expression are relative to control samples. All samples were normalized to β-actin.

```
Primer sequence
Rat MMP-13 gene
5'-GCCCTATCCCTTGATGCCATT-3' (sense)

5'-ACAGTTCAGGCTCAACCTGCTG-3' (antisense)

Rat β-actin
5'-AGCCATGTACGTAGCCATCC-3' (sense)

5'-ACCCTCATAGATGGGCACAG-3' (antisense)
```

Example 1

The inhibitory effect of cranberry extract non-dialyzable material (cranberry extract NDM) on PTH stimulated MMP-13 expression was tested.

The cranberry extract NDM was prepared according to a method described by Weiss, et al. *J. Am. Dent. Assoc.* 129 (12), 1719 (1998). The cranberry extract NDM was obtained by dialyzing cranberry juice through a high molecular weight cut-off dialysis bag. The substance left in the bag that does not dialyze out is the non-dialyzable material (NDM).

Cranberry extract NDM at 10 ppm, 4 ppm and 1 ppm in simple solution showed MMP-13 inhibition activity. The fold change in MMP-13 gene expression relative to the control sample is shown in Table 1.

TABLE 1

|  | Average | Standard deviation |
|---|---|---|
| Negative Control | 1.07 | 0.35 |
| PTH | 72.88 | 2.01 |
| Cranberry 10 ppm | 0.78 | 0.32 |
| Cranberry 4 ppm | 1.22 | 0.15 |
| Cranberry 1 ppm | 2.57 | 1.41 |
| PTH + Cranberry 10 ppm | 33.03 | 11.04 |
| PTH + Cranberry 4 ppm | 46.72 | 9.27 |
| PTH + Cranberry 1 ppm | 54.49 | 5.86 |

The results shown in Table 1 demonstrate that cranberry extract NDM decreases the expression of PTH stimulated MMP-13 gene expression. This suggests that cranberry extract NDM prevents matrix degradation by reducing expression of MMP-13.

Example 2

The inhibitory effect of AKBBA on PTH stimulated MMP-13 expression was tested. AKBBA was purchased from Sabinsa Corporation.

AKBBA at 10 ppm in simple solution showed MMP-13 inhibition activity in Table 2. The fold change in MMP-13 gene expression relative to the control sample is shown in Table 2.

TABLE 2

|  | Average | Standard deviation |
|---|---|---|
| Negative Control | 0.89 | 0.25 |
| PTH | 406.05 | 122.16 |
| AKBBA 10 ppm | 1.45 | 0.62 |
| PTH + AKBBA 10 ppm | 59.77 | 18.33 |

The results shown in Table 2 demonstrate that AKBBA decreases the expression of PTH stimulated MMP-13 gene expression. This suggests that AKBBA prevents matrix degradation by reducing the expression of MMP-13.

Example 3

Resveratrol (3,5,4'-trihydrostilbene) is a polyphenolic compound found in grapes, especially in grape skin and seeds. Resveratrol was purchased from Sabinsa Corporation.

Resveratrol at 100 ppm, 50 ppm, 10 ppm, 1 ppm and 0.1 ppm in simple solution showed MMP-13 inhibition activity (Table 3). The fold change in MMP-13 gene expression relative to the control sample is shown in Table 3.

TABLE 3

|  | Average | Standard deviation |
|---|---|---|
| Negative Control | 0.68 | 0.28 |
| PTH | 54.64 | 6.03 |
| Resveratrol 100 ppm | 1.09 | 0.04 |
| Resveratrol 50 ppm | 0.38 | 0.22 |
| Resveratrol 10 ppm | 0.65 | 0.09 |
| Resveratrol 1 ppm | 0.71 | 0.06 |
| Resveratrol 0.1 ppm | 1.07 | 0.24 |
| PTH + Resveratrol 100 ppm | 0.65 | 0.24 |
| PTH + Resveratrol 50 ppm | 0.91 | 0.79 |
| PTH + Resveratrol 10 ppm | 1.86 | 0.69 |
| PTH + Resveratrol 1 ppm | 19.97 | 1.81 |
| PTH + Resveratrol 0.1 ppm | 46.02 | 5.78 |

The results shown in Table 3 demonstrate that resveratrol decreases the expression of PTH stimulated MMP-13 gene expression. This suggests that resveratrol prevents matrix degradation by reducing expression of MMP-13.

Example 4

Compound A (2-isopropyl-5-methylcyclohexyl 2-hydroxyphenylcarbantate) has a representative structure of Compound A is:

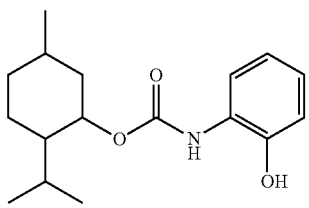 [SMILES: CC1CCC(C(C)C)C(OC(=O)Nc2ccccc2O)C1]

Compound A at 7 ppm in simple solution showed MMP-13 inhibition activity (Table 4). The fold change in MMP-13 gene expression relative to the control sample is shown in Table 4.

TABLE 4

|  | Average | Standard deviation |
| --- | --- | --- |
| Negative control | 1.19 | 0.16 |
| PTH | 445.18 | 111.95 |
| Compound A at 7 ppm | 7.41 | 2.65 |
| PTH + Compound A at 7 ppm | 14.674 | 3.68 |

The results shown in Table 4 demonstrate that Compound A decreases the expression of PTH stimulated MMP-13 gene expression. This suggests that Compound A prevents matrix degradation by reducing expression of MMP-13.

Example 5

Compound B (4-acetamidophenyl 2-isopropyl-5-methyl-cyclohexyl carbonate) has a representative structure of Compound B is:

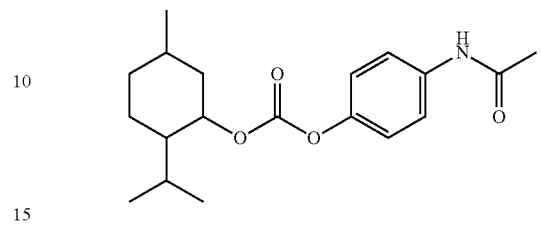

Compound B at 10 ppm in simple solution showed MMP-13 inhibition activity Table 5). The fold change in MMP-13 gene expression relative to the control sample is shown in Table 5.

TABLE 5

|  | Average | Standard deviation |
| --- | --- | --- |
| Negative control | 1.24 | 0.24 |
| PTH | 257.03 | 20.82 |
| Compound B at 10 ppm | 5.78 | 1.94 |
| PTH + Compound B at 10 ppm | 49.86 | 25.03 |

The results shown in Table 5 demonstrate that compound B decreases the expression of PTH stimulated MMP-13 gene expression. Since the level of MMP-13 is correlated to periodontal clinical indexes, this suggests that Compound B prevents matrix degradation by reducing MMP-13 with parathyroid hormone (PTH) stimulation.

What is claimed is:

1. A composition comprising a therapeutically effective amount of a MMP-13 inhibitor, and an orally acceptable carrier, wherein the MMP-13 inhibitor is 4-acetamidophenyl 2-isopropyl-5-methylcyclohexyl carbonate.

2. The composition of claim 1, wherein the composition further comprises an MMP-13 inhibitor selected from the group consisting of cranberry extract non-dialyzable material, acetyl keto β-boswellic acid, resveratrol, and 2-isopropyl-5-methylcyclohexyl 2-hydroxyphenylcarbamate, and combinations thereof.

3. The composition of claim 2, wherein the MMP-13 inhibitor comprises cranberry extract non-dialyzable material.

4. The composition of claim 2, wherein the MMP-13 inhibitor comprises acetyl keto β-boswellic acid.

5. The composition of claim 2, wherein the MMP-13 inhibitor comprises resveratrol.

6. The composition of claim 2, wherein the MMP-13 inhibitor comprises 2-isopropyl-5-methylcyclohex 2-hydroxyphenylcarbamate.

7. The composition of claim 1, wherein the composition is a dentifrice.

8. The composition of claim 7, wherein the dentifrice is selected from the group consisting of: toothpaste; deep striped toothpaste; surface striped toothpaste; multi-layered toothpaste; a gel surrounding toothpaste; powder; beads; mouthwash; mouth rinses; lozenge; dental gel; a periodontal gel; a liquid suitable for painting a dental surface; a chewing gum; a dissolvable, partially dissolvable or non-dissolvable film or strip; a wafer; a wipe or towelette; an implant; a foam; a troche; a dental floss, liquid formulated for oral application in a small portable bottle; liquid formulated for oral application in a small portable drop-generating bottle; a soft pliable tablet; or a combination of two or more thereof.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Rattus norvegicus

<400> SEQUENCE: 1
gccctatccc ttgatgccat t                                           21

<210> SEQ ID NO 2
<211> LENGTH: 22
<212> TYPE: DNA
<213> ORGANISM: Rattus norvegicus

<400> SEQUENCE: 2
acagttcagg ctcaacctgc tg                                          22

<210> SEQ ID NO 3
<211> LENGTH: 20
<212> TYPE: DNA
<213> ORGANISM: Rattus norvegicus

<400> SEQUENCE: 3
agccatgtac gtagccatcc                                             20

<210> SEQ ID NO 4
<211> LENGTH: 20
<212> TYPE: DNA
```

| | |
|---|---|
| <213> ORGANISM: Rattus norvegicus | |
| <400> SEQUENCE: 4 | |
| accctcatag atgggcacag | 20 |